(12) United States Patent
Colantonio et al.

(10) Patent No.: US 8,083,729 B2
(45) Date of Patent: Dec. 27, 2011

(54) APPARATUS AND METHOD FOR STERILE DOCKING OF MALE MEDICAL LINE CONNECTORS

(75) Inventors: Anthony J. Colantonio, Meadville, PA (US); Menno D. Jager, Meadville, PA (US)

(73) Assignee: PSI Medical Catheter Care, LLC, Erie, PA (US)

( * ) Notice: Subject to any disclaimer, the term of this patent is extended or adjusted under 35 U.S.C. 154(b) by 248 days.

(21) Appl. No.: 12/074,951

(22) Filed: Mar. 7, 2008

(65) Prior Publication Data

US 2009/0118708 A1 May 7, 2009

Related U.S. Application Data

(60) Provisional application No. 61/002,173, filed on Nov. 7, 2007.

(51) Int. Cl.
*A61M 25/16* (2006.01)
*A61M 25/18* (2006.01)
*A61M 39/00* (2006.01)
*A61M 39/10* (2006.01)
*A61M 39/02* (2006.01)

(52) U.S. Cl. ........ 604/539; 128/917; 604/533; 604/534; 604/535; 604/905

(58) Field of Classification Search .............. 604/539, 604/538, 415, 905, 411, 533, 256, 246, 500, 604/513, 265, 48, 534, 535, 537, 93.01; 128/917, 128/912, DIG. 6, DIG. 26
See application file for complete search history.

(56) References Cited

U.S. PATENT DOCUMENTS

| | | | |
|---|---|---|---|
| 4,340,148 A | 7/1982 | Beckham | |
| 4,624,664 A * | 11/1986 | Peluso et al. | 604/256 |
| 4,983,161 A | 1/1991 | Dadson et al. | |
| 5,167,643 A | 12/1992 | Lynn | |
| 5,195,957 A | 3/1993 | Tollini | |
| 5,310,524 A * | 5/1994 | Campbell et al. | 422/33 |
| 5,385,372 A | 1/1995 | Utterberg | |
| 5,509,573 A * | 4/1996 | Campoli | 221/133 |
| 5,624,412 A * | 4/1997 | Weekley | 604/539 |
| 5,933,936 A * | 8/1999 | Wand | 29/283 |
| 5,947,937 A * | 9/1999 | Urrutia et al. | 604/533 |
| 6,152,913 A | 11/2000 | Feith et al. | |
| 6,322,551 B1 * | 11/2001 | Brugger | 604/533 |
| 6,485,479 B1 | 11/2002 | Knierbein | |
| 6,684,603 B2 | 2/2004 | Nervo | |
| 7,081,109 B2 | 7/2006 | Tighe et al. | |
| 7,083,605 B2 | 8/2006 | Miyahara | |
| 7,198,611 B2 | 4/2007 | Connell et al. | |
| 2004/0111078 A1 * | 6/2004 | Miyahara | 604/414 |
| 2006/0259013 A1 | 11/2006 | Ranalletta et al. | |

* cited by examiner

*Primary Examiner* — Kevin C Sirmons
*Assistant Examiner* — Shefali Patel
(74) *Attorney, Agent, or Firm* — Carothers and Carothers

(57) ABSTRACT

A docking station for male medical line connectors, including a base housing securable to a stationary surface and having a plurality of docking bays, each of which is dimensioned and contoured for respectively receiving and temporarily retaining ampules containing sterilization fluid. Each of the ampules has a chamber therein containing the sterilization fluid and an access mouth exteriorly exposed when the ampule is secured in one of the bays, and each mouth has a female medical line connection dimensioned and contoured for temporarily receiving and securing a male medical line connector thereto with the tubular tip of the male connector immersed in sterilization fluid during the period of time that the infusion tubing is disconnected from the patient.

12 Claims, 6 Drawing Sheets

APPARATUS AND METHOD FOR STERILE DOCKING OF MALE MEDICAL LINE CONNECTORS

CROSS REFERENCE

This application claims the benefit of U.S. Provisional Application No. 61/002,173, filed on Nov. 7, 2007, and entitled Docking Station for the Temporary Sterile Securement and Simultaneous Disinfection of Medical Infusion Tubing.

FIELD OF THE INVENTION

The present invention relates to the field of medical liquid administration, and more particularly, to a docking apparatus and method for simultaneously enhancing the sterility, temporary securement and disinfection of disconnected medical infusion tubing during periods of non-use.

BACKGROUND OF THE INVENTION

Improvements in patient safety have been among the primary concerns of many efforts in today's healthcare industry. Healthcare associated infections remain a major area of focus for these efforts. The Center for Disease Control and Prevention cites healthcare associated infections in the top ten leading causes of death in the United States. Annually, healthcare associated infections account for an estimated 1.7 million infections in hospitals, 99,000 associated deaths, and 4.5 to 5.7 billion dollars in added patient care costs.

The reduction of healthcare associated infections depends upon awareness and adherence to aseptic technique when handling medical equipment that comes into direct contact with a patient. Medical equipment is constantly threatened by exposure to surrounding contaminated surfaces. These surfaces contain microorganisms (bacteria) which can easily adhere to the surface of medical equipment. Once contaminated, the medical equipment becomes a danger to the patient and can serve as a silent killer. Healthcare institutions use millions of intravenous catheters each year. These catheters are at risk of contamination by a variety of mechanisms. One such mechanism relates to the contamination of the exposed tip of an intravenous administration set. This particular problem arises when an intravenous infusion line is temporarily disconnected from a patient (a process which can occur multiple times per day for an individual patient). During the time that the infusion line is disconnected from the patient, the exposed tip of the intravenous tubing may contact potential contaminants. These contaminants can then lead to infection within a patient's bloodstream once the infusion tubing is reconnected to the patient.

The critical event in the aforementioned circumstance is the failure to retain the sterility of the infusion tubing tip and failure to adequately disinfect the tip in the instance of inadvertent contamination during the time of disconnect from the patient. This risk is, in part, an unanticipated outcome of the somewhat recent implementation of needle-less intravenous systems. Prior to the introduction of these needle-less systems, healthcare practitioners typically replaced the needle used to connect the infusion tubing to the intravenous tubing with a new sterile, capped needle to prevent contamination when the line was hanging between uses. Currently, many practitioners are not actively considering the risk of contamination and are not taking steps to secure the sterility of the exposed tubing. When efforts are made to maintain the sterility of the exposed tubing tip, these efforts are both cumbersome (and therefore at times skipped over), or they fail due to technical shortcomings.

Safe practice recommendations include the use of aseptic technique when handling medical infusion lines. The aseptic technique, as pertains specifically to intravenous catheters, includes covering the exposed end of intravenous tubing used for intermittent infusions with a sterile cap between uses and to disinfect the cap prior to reattachment to a patient. There currently exists a plain sterile cap for intravenous infusion tubing that is individually packaged. These caps have shortcomings which limit their routine use. Specifically, these caps must be opened from their individual wrappers for use. This process itself can place the cap at risk for infection before it is even placed onto the intravenous tubing as it requires significant manipulation by the practitioner. In addition, the practitioner may not have one of the individual wrappers immediately available when needed. Furthermore, these caps do not accomplish any active disinfection of the intravenous tubing tip surface.

Disinfecting the surfaces of medical equipment with alcohol is a well accepted and established practice. Evidence exists supporting the use of a one minute alcohol immersion as adequate disinfectant technique. Current practice often utilizes alcohol cloth swabs to accomplish the task of disinfecting the surface of medial equipment, including intravenous tubing. This method has faults limiting its use. The exposure of the intravenous tubing tip to the cloth swab of alcohol does not qualify as an immersion technique. Also, the practitioner may be very likely to contaminate the tubing tip with their skin which is surrounding the cloth swab as it is being held. Lastly, the alcohol prep pads containing the cloth swabs may not be immediately available for use at the time of greatest need.

The docking station herein disclosed includes a means to temporarily and safely secure the free tip of intravenous tubing (or any other medical infusion line) while simultaneously disinfecting that same tip. In this way, the device and associated method described will adequately provide a means to maintain the sterility of a reusable intravenous administration set (or other medical infusion line) that has been disconnected from a patient until it is ready to be reattached for future use.

SUMMARY OF THE INVENTION

The docking station of the present invention for male medical line connectors, such as, but not limited to, IV connectors, indwelling nerve catheters and dialysate connectors, is comprised of a base housing that is securable to a stationary surface and has a plurality of docking bays. Each of the docking bays are dimensioned and contoured for respectively receiving and temporarily retaining capsules or ampules containing sterilization fluid, such an alcohol liquid or gel. Each of the ampules has a chamber therein containing the sterilization fluid and an access mouth which is exteriorly exposed when the ampule is secured in one of the bays. The mouth of the ampule has a female medical line connection, such as a luer lock mechanism, dimensioned and contoured for temporarily receiving and securing a male medical line connector thereto with the tubular tip of the male connector thereby immersed in the sterilization fluid.

When it is time to reconnect the male medical line connector, it is pulled, along with the connected ampule, from the docking station bay by pulling the connected male connector. Thereafter the male connector is disconnected from the ampule for reconnection to the patient and the used ampule is discarded.

A removable sterilization cover may be provided over each of the bays of the docking station.

The ampules are received respectively in the bays of the docking station by push insert and pull removal. The ampules in a preferred embodiment are respectively received each in a socket provided in the respective bays with a friction fit for retaining the ampules respectively in the bays. This friction fit may also additionally be provided with a snap fit if desired.

The ampules are secured against rotation in the bays whereby the male connectors may be rotatably connected to the respective ampules. To provide this securement against rotation, the ampules and bays have inter-engaging parts whereby the ampules are secured against rotation in the respective bays.

The base housing of the docking station may be slidably received in a holster which in turn is secured to a normally stationary vertical surface, such as an IV pole.

Normally the base will be provided in rows on the base housing and the rows may in addition be designated by color coding to match a corresponding male medical line connector type.

Absorbent material, such as foam, sponge, fiber or fabric, may also be provided in the ampules for absorbing and retaining the sterilization fluid. In addition, the ampule mouths may be sealed with a pierceable membrane for piercing by the tubular tip of the male connector when it is secured to the female connection of the ampule.

BRIEF DESCRIPTION OF THE DRAWINGS

Other objects and advantages appear hereinafter in the following description and claims. The accompany drawings show, for the purpose of exemplification, without limiting the scope of the invention or the appended claims, certain practical embodiments of the present invention wherein:

BRIEF DESCRIPTION OF A PREFERRED EMBODIMENT

Figure 1:
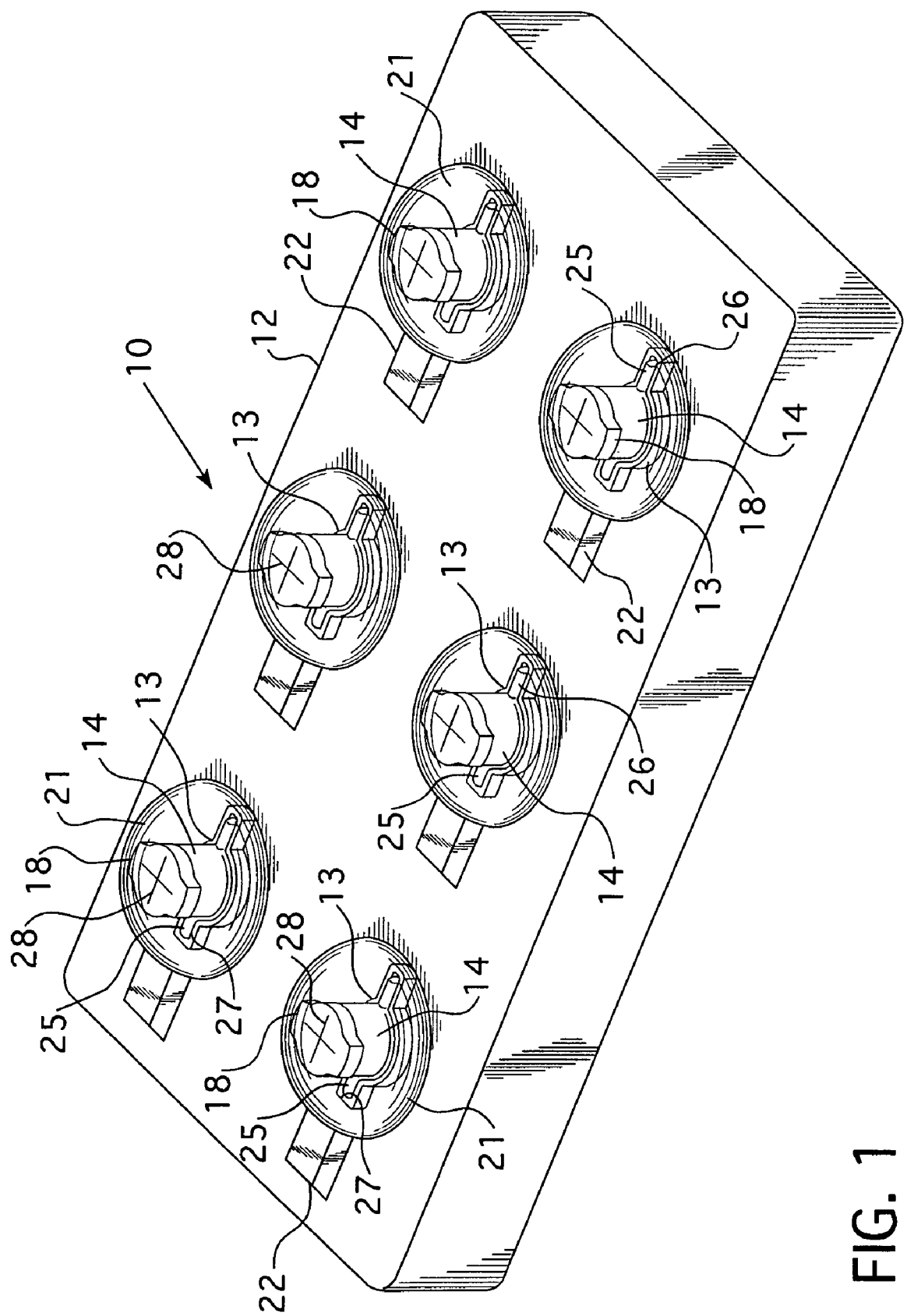
FIG. 1 is a perspective view of the docking station of the present invention showing the base housing with multiple docking bays respectively retaining ampules containing sterilization fluid.

Referring to the drawings, the docking station 10 is provided for docking male medical line connectors 11. The docking station 10 is comprised of a base housing 12, which in this instance is constructed of transparent plastic.

Base housing 12 is provided with a plurality of docking bays 13, each of which is dimensioned and contoured for respectively receiving and temporarily retaining ampules 14 containing sterilization fluid, liquid or gel alcohol. Each of the ampules 14 have a chamber 15 therein containing the sterilization fluid. The chambers 15 contain a foam liquid or gel absorbent material 16 for absorbing and retaining the sterilization fluid. Ampules 14 are each provided with a mouth 17 having a female medical line connector 18 (luer lock) exteriorly exposed when the ampules 14 are secured in one of the respective bays 13. The female medical line connector 18 is dimensioned and contoured for temporarily receiving and securing a male medical line connector 11 thereto with the tubular tip 20 thereof received in the absorbent material 16 thereby immersing the tip in sterilization fluid.

Dome shaped sterilization covers 21 are removable received over each of the bays 13. The covers 21 are also made of transparent plastic and have tabs 22 extending from a circumferential edge. Tabs 22 are provided with a light adhesive whereby each of the covers 21 may be readily removed individually by gripping the respective tab 22 and peeling it away from the upper surface 23 of base housing 12.

Each of the ampules 14 are received respectively in bays 13 by push insert and pull removal. Ampules 14 are respectively received in a socket 24 provided in each of the bays 13 for retaining the ampules 14 in bays 13 with a friction snap fit.

The ampules 14 are secured against rotation in bays 13 whereby the male connectors 11 may be rotatably connected with a conventional rotational luer lock to the ampules 14 while the ampules 14 remain secured in their respective bays 13. This is accomplished by providing the ampules 14 and the respective bays 13 with inter-engaging parts 25 whereby the ampules 14 are secured against rotation in the bays 13.

These inter-engaging parts 25 consist of wings 26 radially extending from the ampules 14, which in turn are received in corresponding grooves 27 of each bay 13.

The mouths 17 of each ampule 14 are sealed with a pierceable membrane 28 for piercing by the tubular tip 20 of male connector 11 in order to help maintain the internal cavity 15 of ampule 14 in a sterile condition and to also help prevent evaporation of the sterilization fluid, such as alcohol. When membrane 28 is pierced it is caused to annularly penetrate into chamber 15 and thereby secure and maintain absorbent material 16 therein.

The docking station 10 is slidably received in a holster 30, which in turn is removably secured to housing 31, which in turn is secured to a vertical surface or support in the form of IV pole 32. The holster 30, or an extra one thereof, may instead be secured to another or different adjacent surface.

Figure 2:
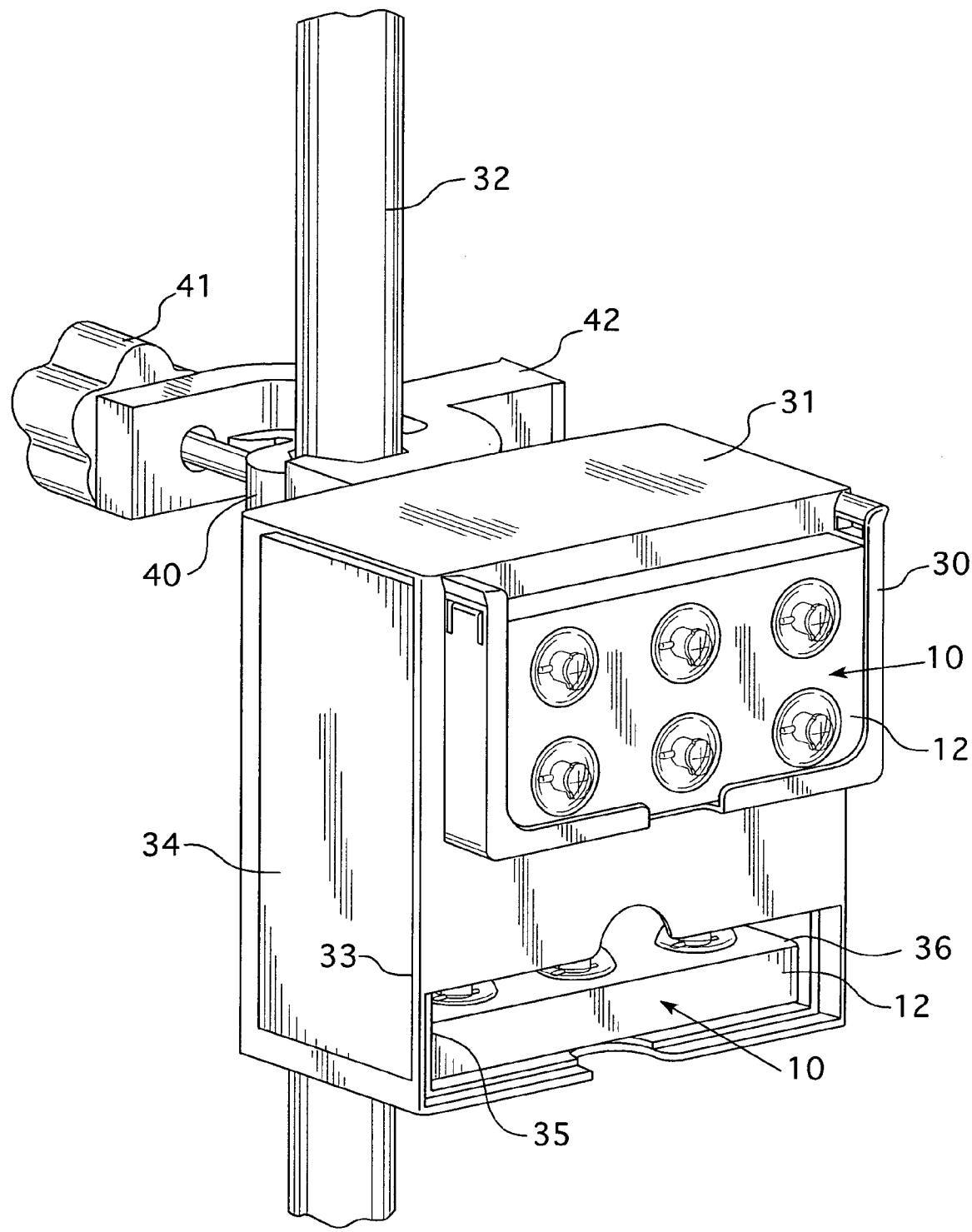
FIG. 2 is a perspective view of the docking station of the present invention as retained in a holster which in turn is secured to a vertically extending IV pole.
Figure 3:
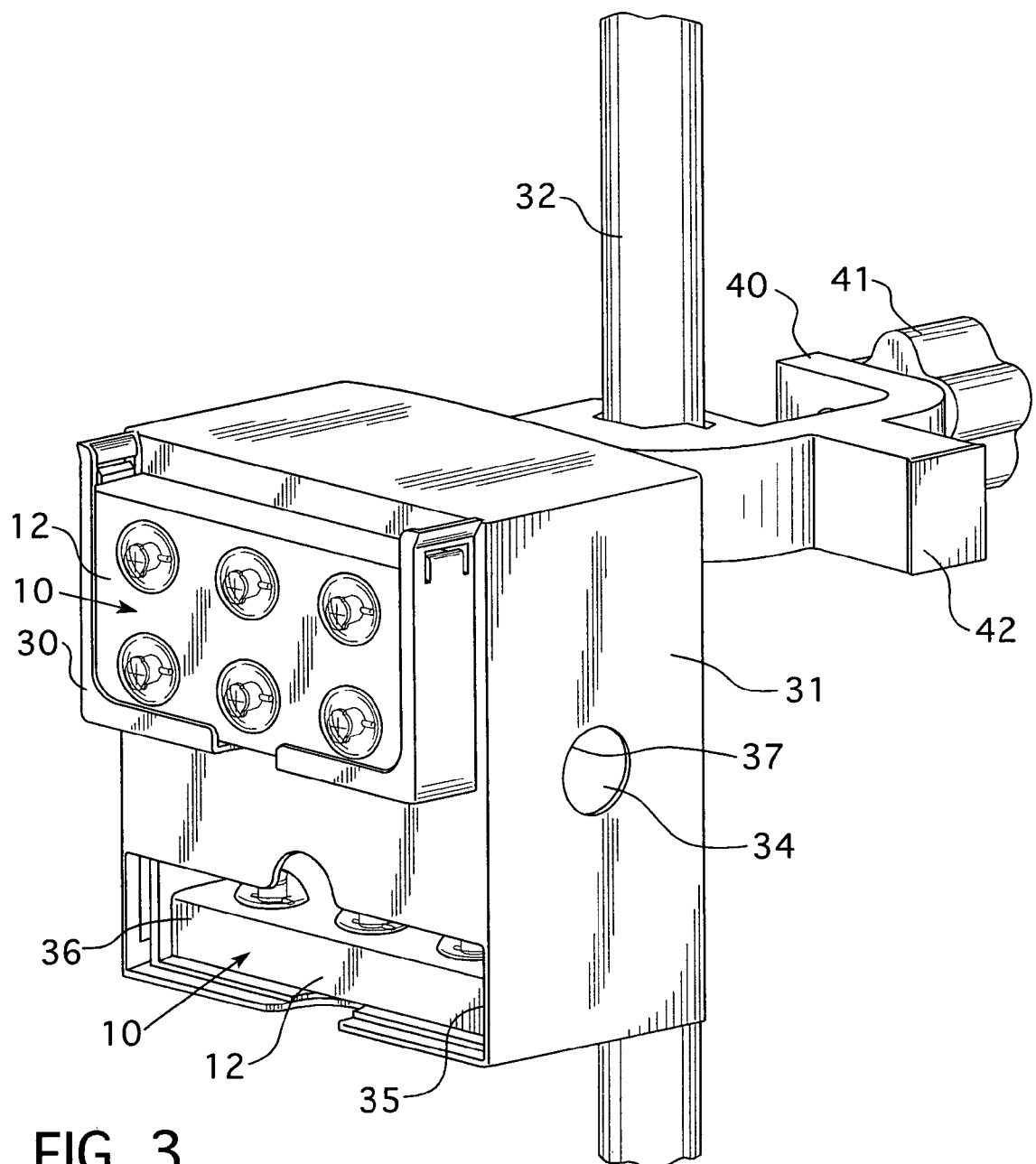
FIG. 3 is a perspective view illustrating the apparatus shown in FIG. 2 as viewed from the opposite side.
Figure 4:
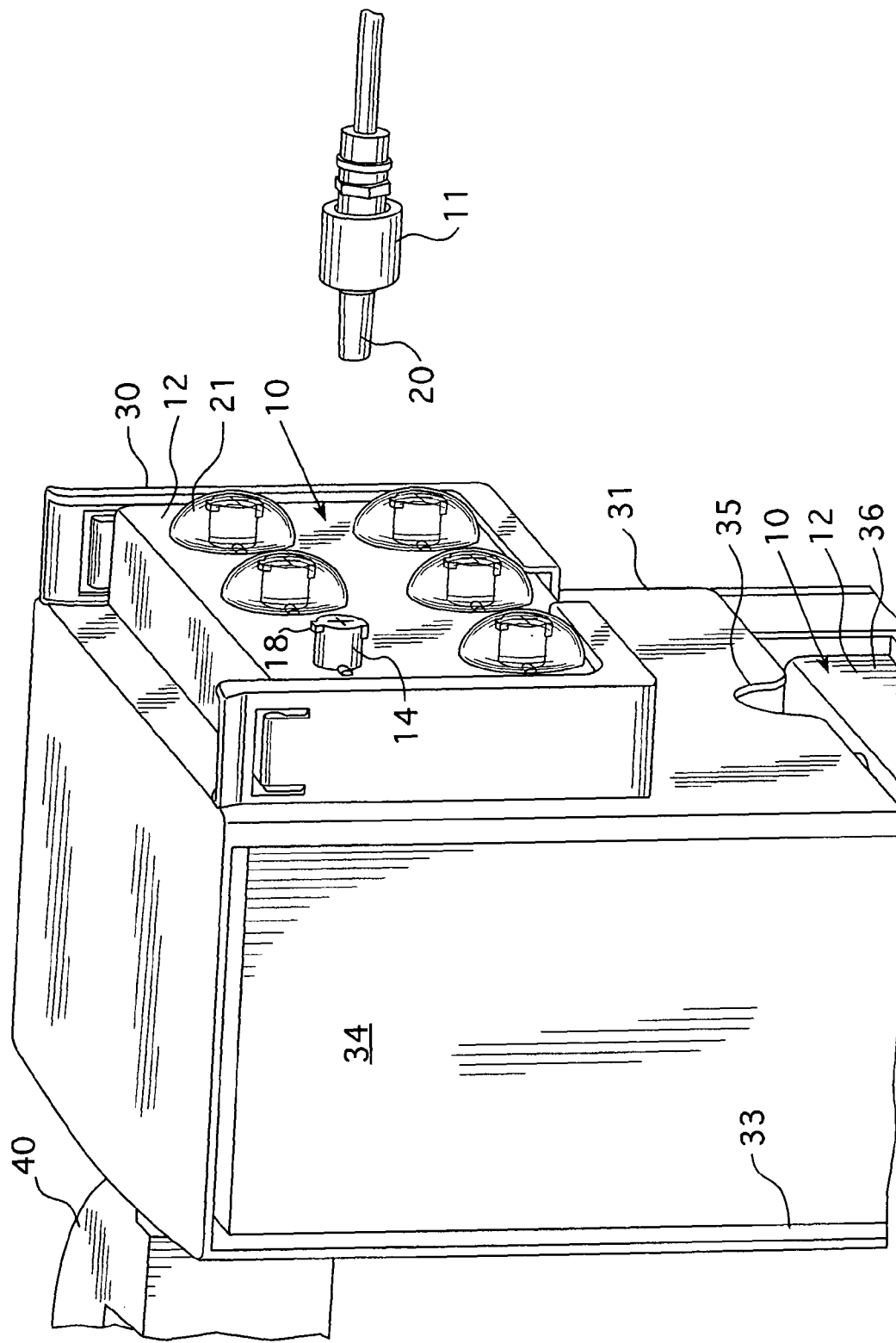
FIG. 4 is a perspective view illustrating a portion of the apparatus shown in FIG. 3 just prior to connection of a male medical line connector to an ampule retained in the docking station.
Figure 5:
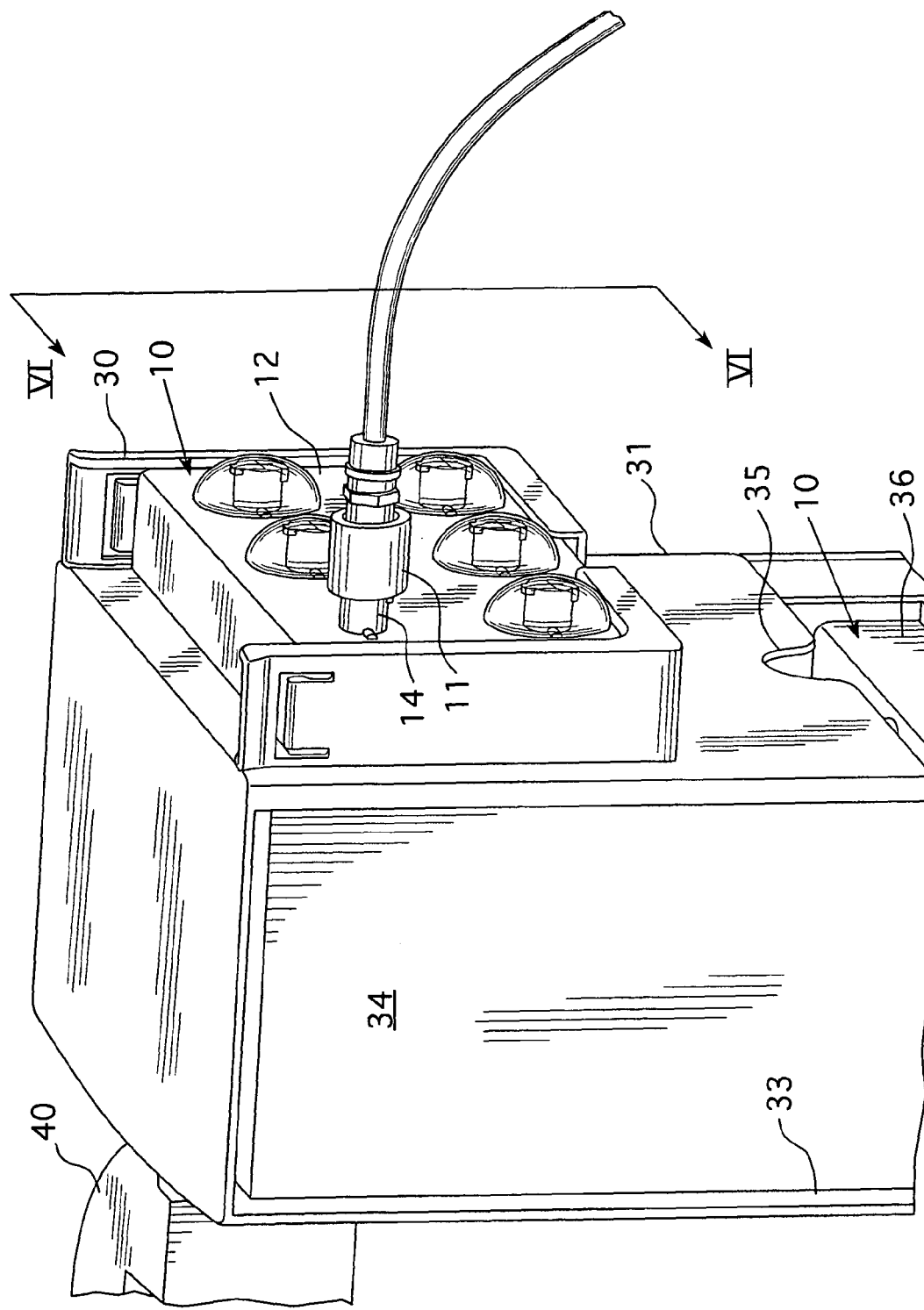
FIG. 5 is an illustration of the apparatus shown in FIG. 4 with the male medical line connectors engaged with an ampule retained in the docking station.
Figure 6:
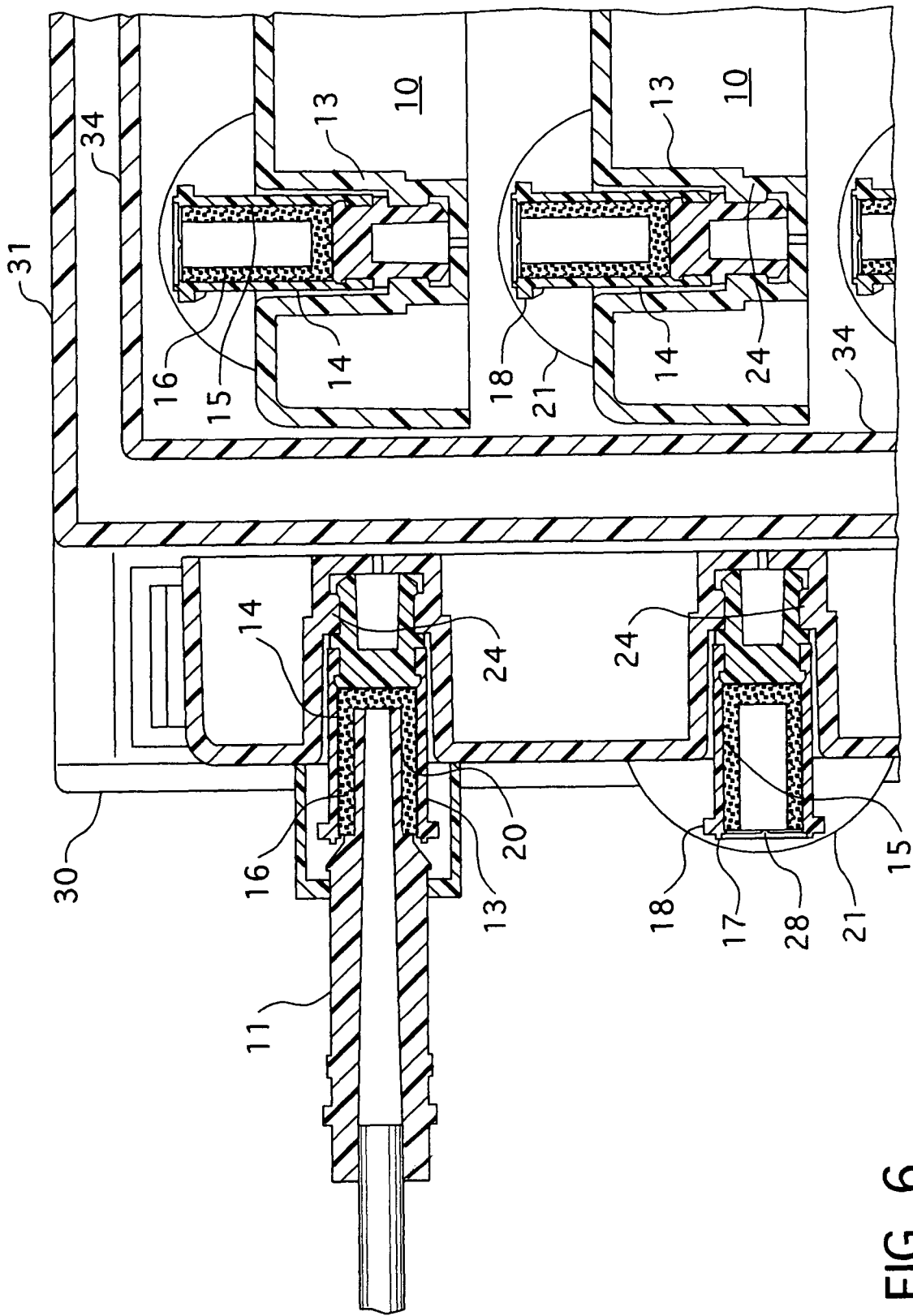
FIG. 6 is an enlarged sectional view of the apparatus illustrated in FIG. 5 as seen along section line VI-VI.

With particular reference to FIGS. 2 and 3, the housing 31 is provided with an internal cavity 33 for slidably receiving therein from the left side, as is best seen in FIG. 2, cartridge housing 34, which is open to the front and contains a stack of the docking stations 10. Housing 31 at the lower front thereof is provided with an opening 35 for thereby permitting access to the stack of docking stations whereby the bottom most docking station 36 in the stack may be removed and placed into the holster 30 when the docking station 10 previously contained therein has been depleted and is need of change.

As is best seen in FIG. 3, housing 31 on the right side is provided with an opening 37 to provide finger hole access in order to push cartridge housing 34 out to the left from the cavity 33 for removal once all of the docking stations 10 therein have been removed.

Housing 31 is secured to vertical IV pole 32 by means of the clamp 40 which is engaged and disengaged in a conventional fashion by rotating knob 41. Clamp 40 is also provided with an extension 42 for attaching or securing accessories, such as another holster 30.

Each of the bays 13 are provided in rows as indicated and, if desired, each of the rows of the base housing 12 may be designated by a different color coding in order to match a corresponding color coding on male medical line connectors 11 of a different type.

Other than the IV pole 32 and parts of the clamp 40, the entire system may be manufactured of plastics.

We claim:

1. A docking station for male medical line connectors having a medical line secured thereto, comprising:

a vertically oriented base housing securable to a normally stationary surface and having a front generally vertical face with an array of a plurality of forwardly open and generally laterally extending docking bays, each of which is dimensioned and contoured for respectively receiving and temporarily retaining therein, with a push insert and a pull removal friction fit, independently accessible ampules containing sterilization fluid;

each of said ampules having a chamber therein containing the sterilization fluid and an access mouth having a temporary seal thereover for retaining said fluid therein and exteriorly exposed when said ampule is secured in one of said bays, said mouth having a female medical line connection dimensioned and contoured for temporarily receiving and securing a male medical line connector thereto with a tubular tip of said male medical line connector thereby immersed in said sterilization fluid, whereby said ampules are independently accessible by respect of said male medical line connectors for sterilized docking of said male medical line connectors independently of each other.

2. The docking station of claim 1, including a removable sterilization cover over each of said bays.

3. The docking station of claim 1, wherein said ampules are respectively received in a socket provided in each of said bays with a friction fit for retaining said ampules respectively in said bays.

4. The docking station of claim 1, wherein said ampules are secured against rotation in said bays whereby said male medical line connectors may be rotatably connected to said ampules.

5. The docking station of claim 4, wherein said ampules and bays have inter-engaging parts whereby said ampules are secured against rotation in said bays.

6. The docking station of claim 1, wherein said base housing is slidably received in a holster which is securable to a vertical surface.

7. The docking station of claim 6, wherein said holster is securable to an IV pole.

8. The docking station of claim 6, including a housing having a chamber therein for storing a plurality of said base housings, and an access in said housing for sequentially removing base housings from said chamber, said holster secured to said housing.

9. The docking station of claim 8, wherein said housing is securable to an IV pole.

10. The docking station of claim 1, wherein said bays are provided in rows on said base housing and said rows are designated by color coding to match a corresponding male medical line connector type.

11. The docking station of claim 1, including absorbent material in said ampules for absorbing and retaining said sterilization fluid.

12. The docking station of claim 1, wherein said temporary seal is a pierceable membrane for piercing by said tubular tip when said male medical line connector is secured to said female medical line connection.

\* \* \* \* \*